(12) United States Patent
Jiao et al.

(10) Patent No.: US 10,550,109 B2
(45) Date of Patent: Feb. 4, 2020

(54) CRYSTAL FORM OF BREXPIPRAZOLE AND PREPARATION METHOD THEREFOR

(71) Applicants: Zhejiang Huahai Pharmaceutical Co., Ltd, Taizhou (CN); Shanghai Aobo Pharmtech, Inc., Ltd., Shanghai (CN)

(72) Inventors: Yinglu Jiao, Shanghai (CN); Handa Li, Shanghai (CN); Boyu Wang, Shanghai (CN); Luning Huang, Shanghai (CN); Xi Chen, Shanghai (CN); Hong Gu, Shanghai (CN)

(73) Assignees: Zhejiang Huahai Pharmaceutical Co., Ltd, Taizhou (CN); Shanghai Aobo Pharmtech, Inc., Ltd., Shanghai (CN)

( * ) Notice: Subject to any disclaimer, the term of this patent is extended or adjusted under 35 U.S.C. 154(b) by 0 days.

(21) Appl. No.: 16/300,301

(22) PCT Filed: May 12, 2017

(86) PCT No.: PCT/CN2017/084171
§ 371 (c)(1),
(2) Date: Nov. 9, 2018

(87) PCT Pub. No.: WO2017/194002
PCT Pub. Date: Nov. 16, 2017

(65) Prior Publication Data
US 2019/0119262 A1    Apr. 25, 2019

(30) Foreign Application Priority Data
May 12, 2016 (CN) .......................... 2016 1 0316062

(51) Int. Cl.
*C07D 409/14* (2006.01)

(52) U.S. Cl.
CPC ........ *C07D 409/14* (2013.01); *C07B 2200/13* (2013.01)

(58) Field of Classification Search
CPC .. C07B 2200/13; C07D 409/12; C07D 409/14
See application file for complete search history.

(56) References Cited

FOREIGN PATENT DOCUMENTS

| CN | 105461703 | 4/1916 | |
|----|-----------|--------|---|
| CN | 105461704 | 4/1916 | |
| CN | 101155804 | 4/2008 | |
| CN | 103717587 | 4/2014 | |
| CN | 104254530 | * 12/2014 | .......... C07D 409/12 |
| CN | 104829602 | 8/2015 | |
| CN | 104844585 | 8/2015 | |
| CN | 104844586 | 8/2015 | |
| CN | 105061414 | 11/2015 | |
| CN | 105175401 | 12/2015 | |
| JP | 2006316052 | 11/2006 | |
| JP | 2014523852 | 9/2014 | |
| JP | 2015514677 | 5/2015 | |
| WO | WO 2013/162046 | 10/2013 | |

OTHER PUBLICATIONS

International Search Report and Written Opinion issued in International Patent Application No. PCT/CN2017/084171, dated Jul. 14, 2017.
Office Action issued in corresponding Japanese Patent Application 2018559341, dated Sep. 11, 2019 (English machine translation).

* cited by examiner

*Primary Examiner* — Erich A Leeser
(74) *Attorney, Agent, or Firm* — Norton Rose Fulbright US LLP

(57) ABSTRACT

Disclosed are a crystal form of brexpiprazole and a preparation method therefor. The X-ray powder diffraction pattern, which is detected with Cu—Kα radiation, of the crystal form of brexpiprazole has characteristic peaks at the positions where 2θ is about 9.1±0.2, 15.2±0.2, 15.7±0.2, 17.6±0.2, 18.1±0.2, 24.4±0.2. The crystal form I of brexpiprazole has a high purity, good stability and good reproducibility, and is suitable for industrial production.

7 Claims, 6 Drawing Sheets

CRYSTAL FORM OF BREXPIPRAZOLE AND PREPARATION METHOD THEREFOR

CROSS-REFERENCE TO RELATED APPLICATIONS

This application is a national phase under 35 U.S.C. § 371 of International Application No. PCT/CN2017/084171, filed May 12, 2017, which claims the priority of the Chinese Patent Application No. 201610316062.2, with the title of "Novel Crystal Form of Brexpiprazole And Preparation Method Therefor", filed on May 12, 2016 before the State Intellectual Property Office of China, each of which are hereby incorporated by reference in their entirety.

FIELD OF THE INVENTION

The present invention relates to a crystal form of brexpiprazole and preparation method therefor.

BACKGROUND OF THE INVENTION

The chemical name of brexpiprazole is 7-{4-[4-(1-benzothiophen-4-yl)piperazin-1-yl]butoxy}-1H-quinolin-2-one, and its structural formula is as shown in formula I:

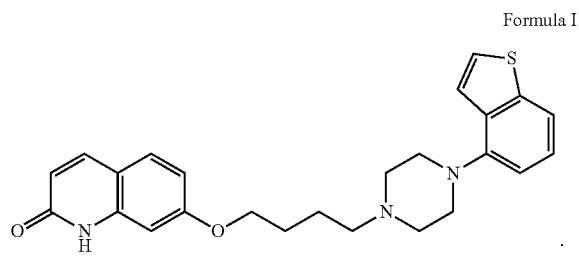 [SMILES: O=c1ccc2ccc(OCCCCN3CCN(c4cccc5sccc45)CC3)cc2[nH]1]

Formula I

In dopamine D2 receptors, D2 receptor partial agonist can cause functional antagonism to mesolimbic pathway and effectively improve positive symptoms caused by overactive D2 in schizophrenia, while causing functional agonism to mesocortical pathway and improving negative symptoms and cognitive impairment caused by depressed D2 function. Brexpiprazole jointly developed by Lundbeck Pharmaceutical (License) and Otsuka Pharmaceutical (original research) is an experimental serotonin-dopamine activity regulator (SDAM) and it's a medicament for treatment of mental disorders with a novel multi-target mechanism. In addition to the main dopamine D2 receptor partial agonism, brexpiprazole also has D3 receptor partial agonism, 5-HT1A partial receptor partial agonism and 5-HT2A receptor partial antagonism. Therefore, it is a novel medicament with anti-schizophrenic and antidepressive effect, developed against multiple targets of monoamine neurotransmitter.

In recent years, the polymorphism of drug molecules has attracted more and more attention. The preparation method of dihydrated form of brexpiprazole (the XRPD pattern thereof is shown in FIGS. 3 and 4) and anhydrous form of brexpiprazole (the XRPD pattern thereof is shown in FIG. 5) are reported in the patent applications CN 104254530A and WO 2013/162046. Amorphous brexpiprazole (the XRPD pattern thereof is shown in FIG. 6) and preparation method thereof are reported in CN 201510180947.

SUMMARY OF THE INVENTION

The invention discloses a crystal form I of a brexpiprazole compound with good stability, high purity and good reproducibility and a preparation method therefor. The present invention provides a novel crystal form I of brexpiprazole (Formula I) with an X-ray powder diffraction pattern as shown in FIG. 1, which comprises the characteristic peaks of 9.1±0.2, 15.2±0.2, 15.7±0.2, 17.6±0.2, 18.1±0.2, 18.6±0.2, 24.4±0.2 degrees 2θ,

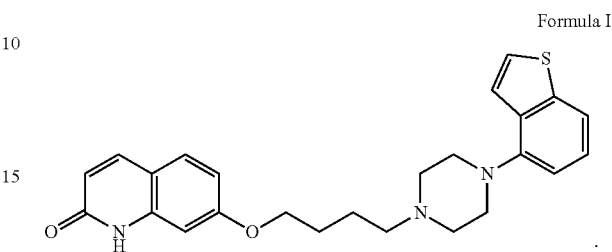

Formula I

In one embodiment, the crystal form I of brexpiprazole according to the present invention has a crystal water endothermic peak at about 43° C.-72° C. and a melting endothermic peak at 179° C.-184° C. as shown in FIG. 2 (differential scanning calorimetry pattern).

In another embodiment, the crystal form I of brexpiprazole according to the present invention has a water content of 3.0 wt. %-4.0 wt. %.

The invention also provides a method for preparing the crystal form I of brexpiprazole, comprising following steps:

(a) mixing brexpiprazole with a mixed solvent of ethanol and water at room temperature to prepare a suspension;

(b) adding acetic acid into the suspension of step (a) and heating to completely dissolved to obtain a clarified solution;

(c) adding the clarified solution of step (b) into quantitative sodium hydroxide solution to pH of 7-14 after cooling, for example, cooling to −5° C.-5° C., precipitating solid, keeping stirring, filtering and drying to obtain the crystal form I of brexpiprazole.

According to the method of the present invention, in one embodiment, a ratio of ethanol to water is 2:3.

According to the method of the present invention, in another embodiment, the clarified solution of step (b) is added into sodium hydroxide solution to pH of 10-11 after cooling in step (c).

The inventors have screened and then obtained the novel crystal form I of brexpiprazole, which is different from the anhydrous and dihydrated crystal forms of brexpiprazole, having a good stability, high purity and good reproducibility, as well as wide application prospects. The method for preparing the novel crystal form I of brexpiprazole provided by the present invention has the advantages of simple operation and good reproducibility, and the obtained product has high purity, good stability and good reproducibility, and it's suitable for large-scale industrial production.

DETAILED DESCRIPTION OF THE INVENTION

The following examples are intended to illustrate the invention without limiting the invention.

The analytical detection conditions of the present invention are as follows:

1. X-ray powder diffraction data was measured using BRUKER D8 Advance from Bruker, Germany, with the conditions of voltage: 40 kV, current: 40 mA; goniometer: vertical goniometer, radius: 280 mm; slit: DS=2°, SS=½°, mask=15 mm, RS=5.0 mm; detector: LYNXEYE detector; scanning mode: continuous scanning; scanning range: 3°-40° 2θ; counting time per step: 0.2 s; total scanning time: 390 s.

2. Differential scanning calorimetry was carried out by using NETZSCH DSC 200 F3 Maia from NETZSCH, Germany, with the conditions of 120 ml/min N2 and the heating rate of 10° C./min.

Example 1

At room temperature, 0.5 g of brexpiprazole free base was weighed into a mixture of 10 ml of ethanol and 15 ml of water to prepare a suspension. 0.275 g of acetic acid was added into the suspension, and the temperature was raised to 70° C.-75° C. to obtain a clarified solution. The clarified solution was cooled to −5° C.-5° C., added to 3.7 ml of 25% aqueous sodium hydroxide solution to precipitate solid, and kept stirring for 1 hour. The temperature was raised to 20° C.-30° C. (pH=11) and stirring was continued for 3-4 hours. Then, suction filtration was performed, and the filter cake was rinsed with water until the pH of the filtrate was 7 and dried to obtain an off-white novel crystal form I of brexpiprazole free base (purity: 98.7%, moisture: 3.3%, ethanol<500 ppm, acetic acid<400 ppm, MS: 433).

$^1$H-NMR (DMSO-$d_6$, 400 M): 1.57-1.64 (m, 2H); 1.73-1.82 (m, 2H); 2.39-2.43 (t, 2H); 2.58 (m, 4H); 3.03 (m, 4H); 4.01-4.04 (t, 2H); 6.25-6.28 (d, 1H); 6.76-6.78 (m, 2H); 6.84-6.86 (d, 1H); 7.22-7.26 (t, 1H); 7.36-7.37 (d, 1H); 7.51-7.53 (d, 1H); 7.57-7.59 (d, 1H); 7.65-7.67 (d, 1H); 7.76-7.78 (d, 1H); 11.55 (s, 1H)

Example 2

At room temperature, 5 g of brexpiprazole free base was weighed into a mixture of 100 ml of ethanol and 150 ml of water. 2.75 g of acetic acid was added, and the temperature was raised to 70° C.-75° C. to obtain a clarified solution. The clarified solution was cooled to −5° C.-5° C., added to 37 ml of 25% aqueous sodium hydroxide solution to precipitate solid, and kept stirring for 1 hour. The temperature was raised to 20° C.-30° C. (pH=11) and stirring was continued for 3-4 hours. Then, suction filtration was performed, and the filter cake was rinsed with water until the pH of the filtrate was 7 and dried to obtain an off-white novel crystal form I of brexpiprazole free base, with the purity of 99.1%.

Comparative Example 1

The dihydrated crystal form of brexpiprazole was prepared using the method of CN104254530A in this comparative example, and the specific method is as follows.

Figure 1:
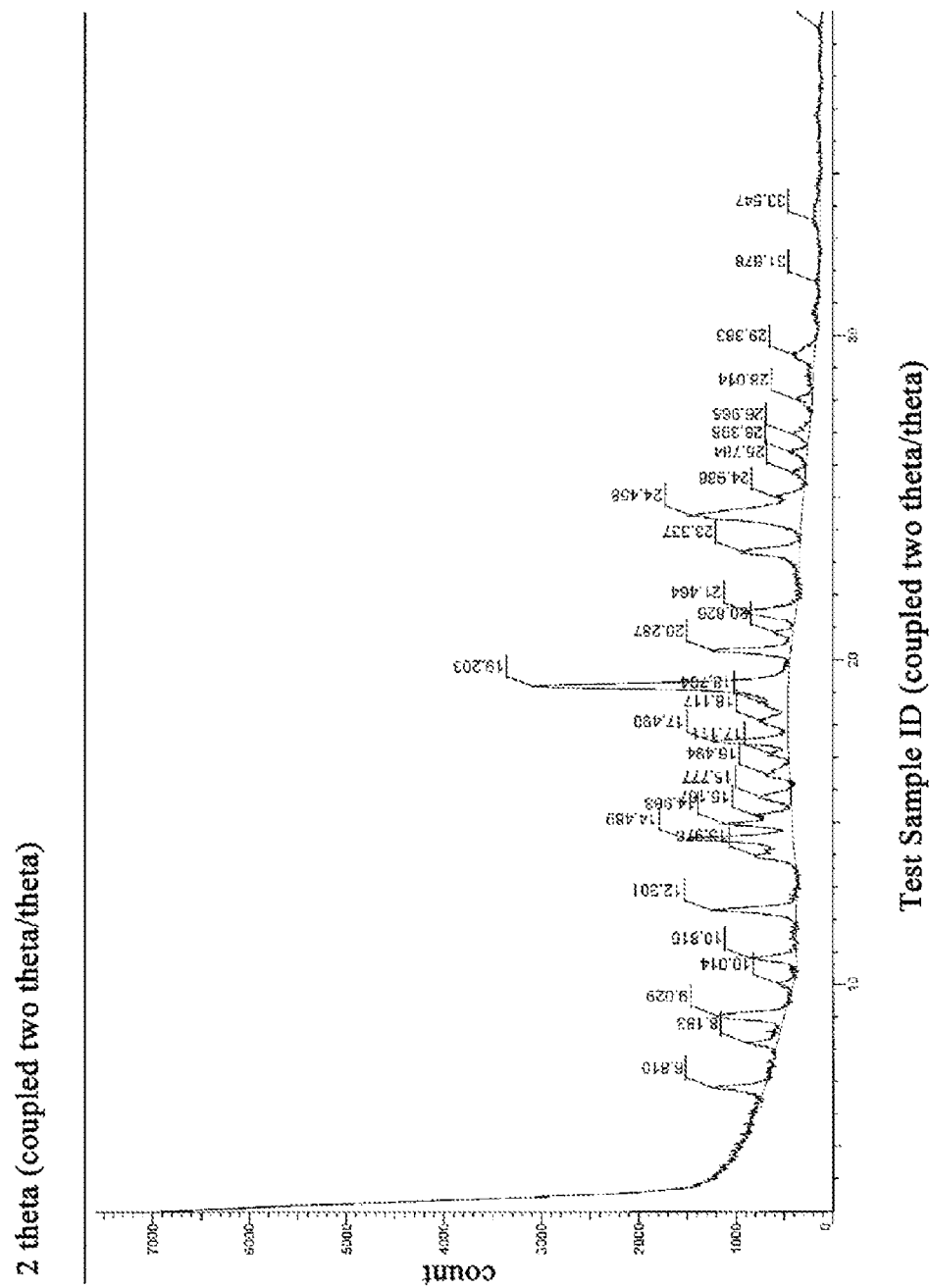
FIG. 1 is an X-ray powder diffraction (XRPD) pattern of a novel crystal form I of brexpiprazole free base obtained according to Example 1 of the present invention.
Figure 2:
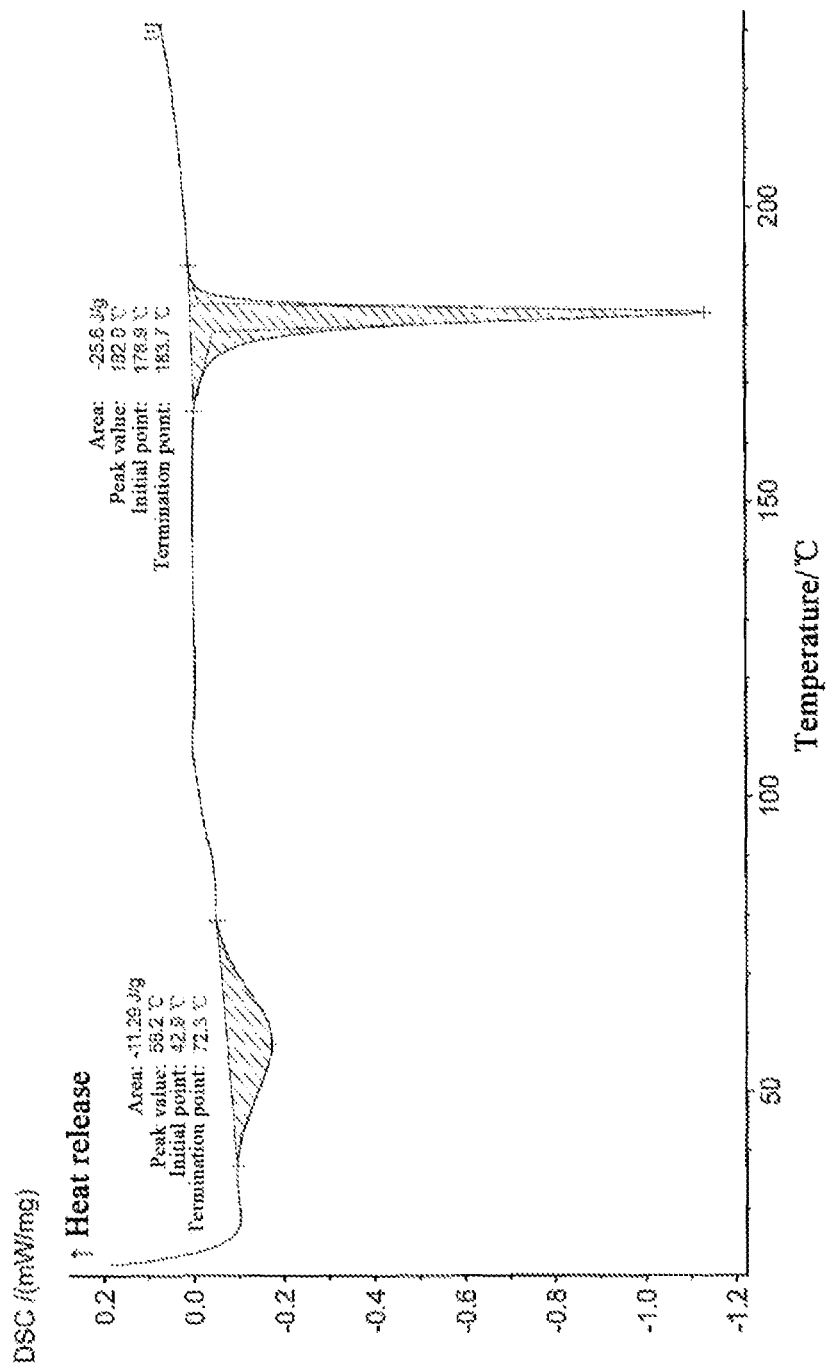
FIG. 2 is a differential scanning calorimetry (DSC) pattern of a novel crystal form I of brexpiprazole free base obtained according to Example 1 of the present invention.
Figure 3:
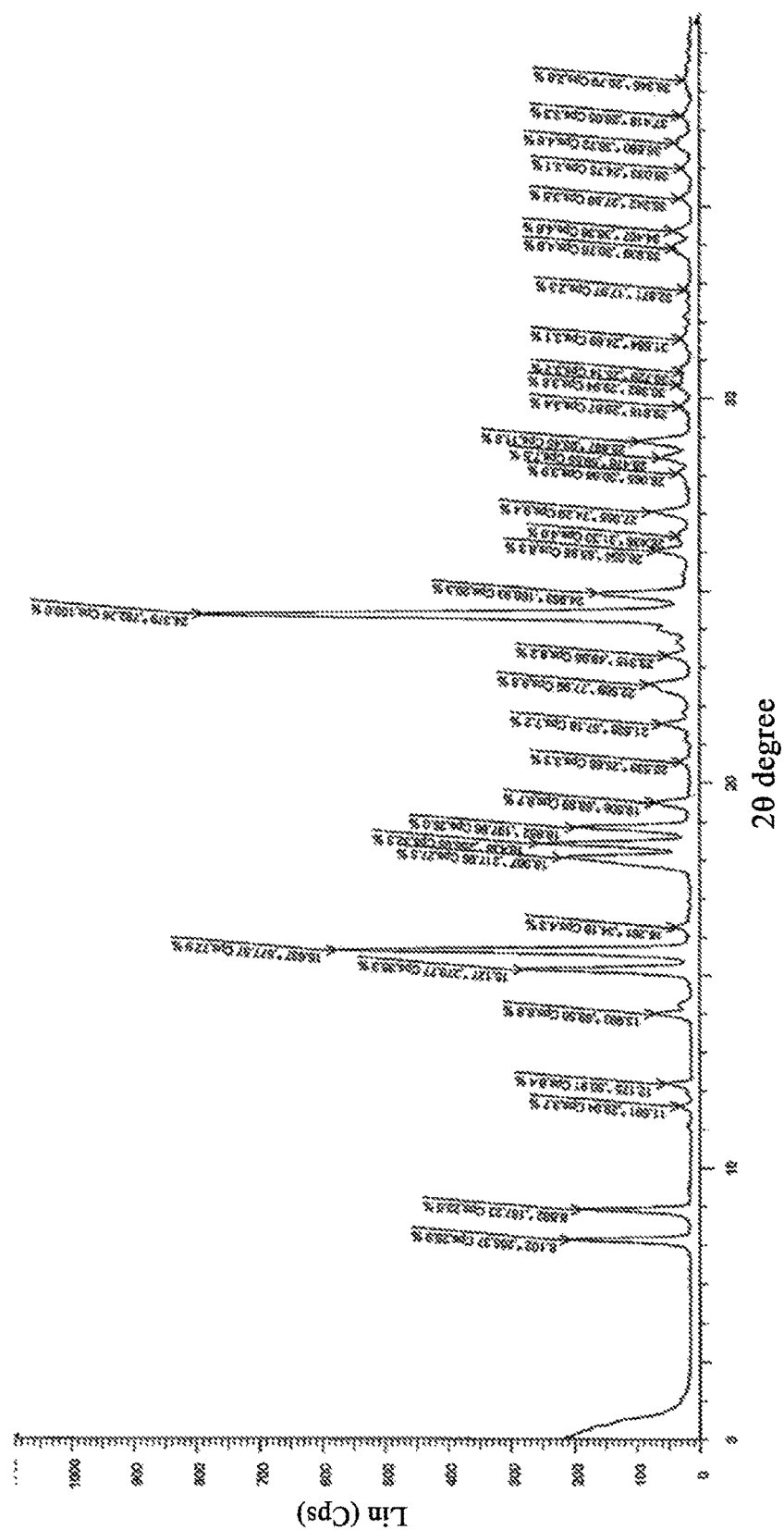
FIG. 3 is an X-ray powder diffraction (XRPD) pattern of a dihydrated crystal form I of brexpiprazole free base reported in CN 104254530A.
Figure 4:
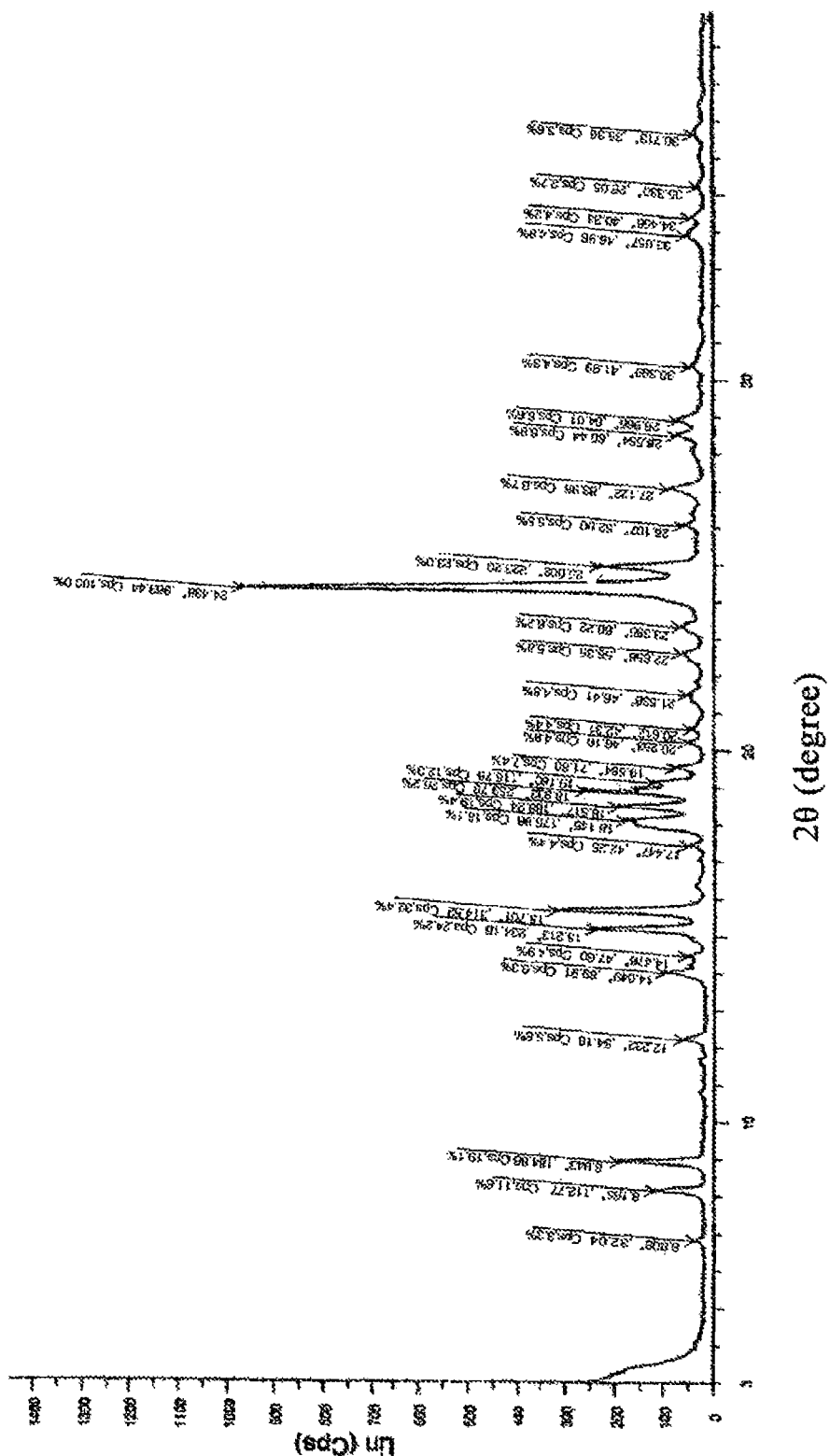
FIG. 4 is an X-ray powder diffraction (XRPD) pattern of a dihydrated crystal form II of brexpiprazole free base reported in CN 104254530A.

Brexpiprazole (7-[4-(4-benzo[b]thiophen-4-yl-piperazin-1-yl)butoxy]-1H-quinolin-2-one, 3.2 kg), ethanol (64 L), water (74 L) and acetic acid (1.77 kg) were mixed in a reactor to prepare an acidic liquid mixture. The mixture was stirred under reflux to dissolve 7-[4-(4-benzo[b]thiophen-4-yl-piperazin-1-yl)butoxy]-1H-quinolin-2-one (reflux temperature: 84° C.). After cooling to −5° C., the solution obtained above was added, over a period of 30 minutes, into a solution containing 25% sodium hydroxide (5.9 kg) and water (54 L) that was cooled to 0° C., to prepare a liquid mixture having a pH of 10. After being stirred at 5° C. or below for one hour, the mixture was heated to 20° C.-30° C. and kept stirring for seven hours. The precipitated crystal was filtered and washed with water (320 L) until alkali in the solid component disappeared (i.e., until the pH of the filtrate became 7). The solid component was then air-dried until its weight remained constant to obtained a white solid of 7-[4-(4-benzo[b]thiophen-4-yl-piperazin-1-yl)butoxy]-1H-quinolin-2-one dihydrate (unground, 3.21 kg). FIG. 3 shows an X-ray powder diffraction pattern of the dihydrate prepared by the above method.

Comparative Example 2

The anhydrous crystal form of brexpiprazole was prepared using the method of CN201510180947.X in this comparative example, and the specific method is as follows.

Figure 5:
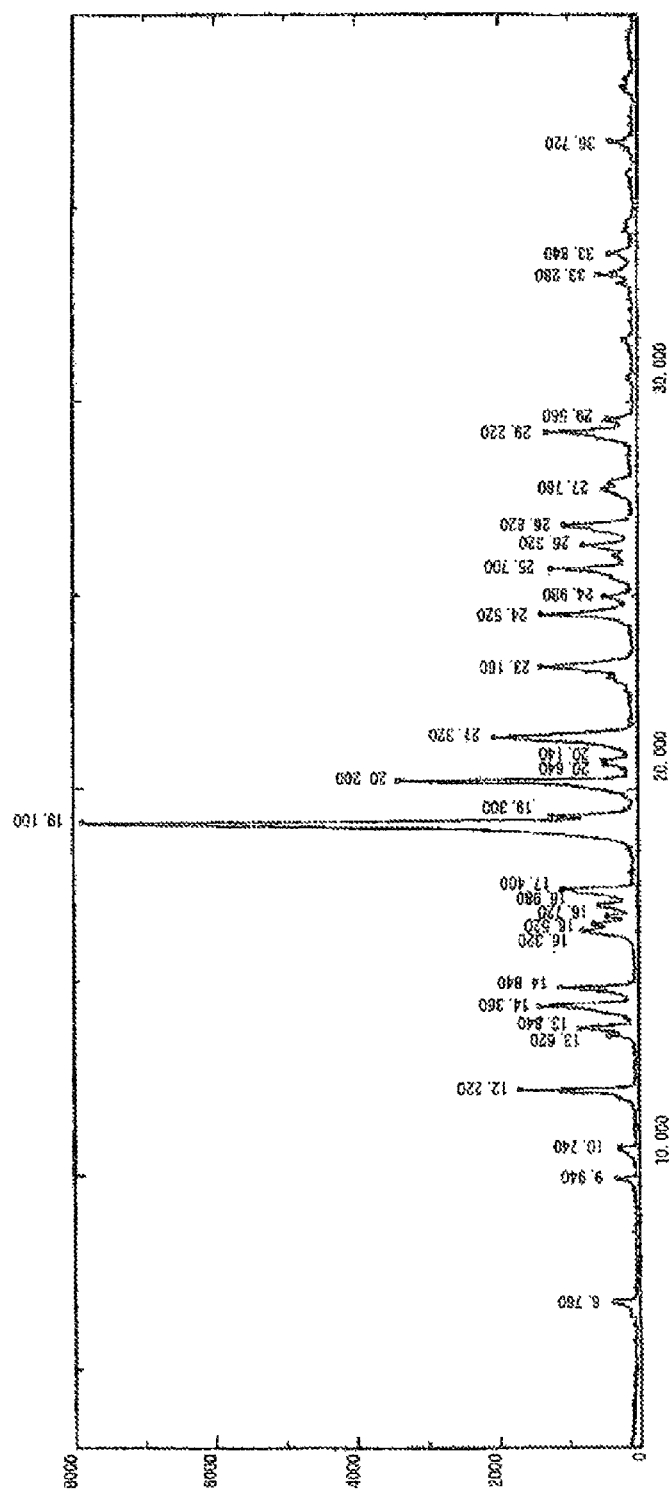
FIG. 5 is an X-ray powder diffraction (XRPD) pattern of an anhydrous crystal form of brexpiprazole free base reported in CN 104254530A.

7-[4-(4-benzo[b]thiophen-4-yl-piperazin-1-yl)butoxy]-1H-quinolin-2-one (700 g), ethanol (14 L) and acetic acid (1.4 L) were mixed in a reactor. The mixture was heated to reflux temperature (76° C.) so that 7-[4-(4-benzo[b]thiophen-4-yl-piperazin-1-yl)butoxy]-1H-quinolin-2-one was dissolved. Concentrated hydrochloric acid (158 mL) was further added to the reactor, the mixture was cooled to 10° C. with stirring. Thereafter, the mixture was heated again, stirred under reflux for one hour, and then cooled to 8° C. The precipitated solid was filtered by suction and washed with ethanol (0.7 L). The solid component was then dried at 60° C. until its weight remained constant to obtained a white solid of 7-[4-(4-benzo[b]thiophen-4-yl-piperazin-1-yl)butoxy]-1H-quinolin-2-one hydrochloride (814 g). The 7-[4-(4-benzo[b]thiophen-4-yl-piperazin-1-yl)butoxy]-1H-quinolin-2-one hydrochloride (800 g), ethanol (7.2 L) and water (4.8 L) were mixed in a reactor, and the mixture was heated to reflux temperature (80° C.) with stirring. After hot filtration, the mixture was again heated to 78° C. to dissolve the precipitated crystal. A solution containing sodium hydroxide (81.6 g) dissolved in water (240 mL) was poured into the solution obtained as above, and the mixture was stirred under reflux for 30 minutes. Water (2.4 L) was added to the mixture, which was then cooled to 40° C. with stirring. The precipitated crystal was filtered and washed with water (16 L). The solid was dried at 80° C. to obtain a white solid of anhydride of 7-[4-(4-benzo[b]thiophen-4-yl-piperazin-1-yl)butoxy]-1H-quinolin-2-one (637 g). The X-ray powder diffraction pattern of the anhydrous crystal form of solid obtained was detected and shown in FIG. 5.

Comparative Example 3

The amorphous form of brexpiprazole was prepared using the method of CN201510180947.X in this comparative example, and the specific method is as follows.

Figure 6:
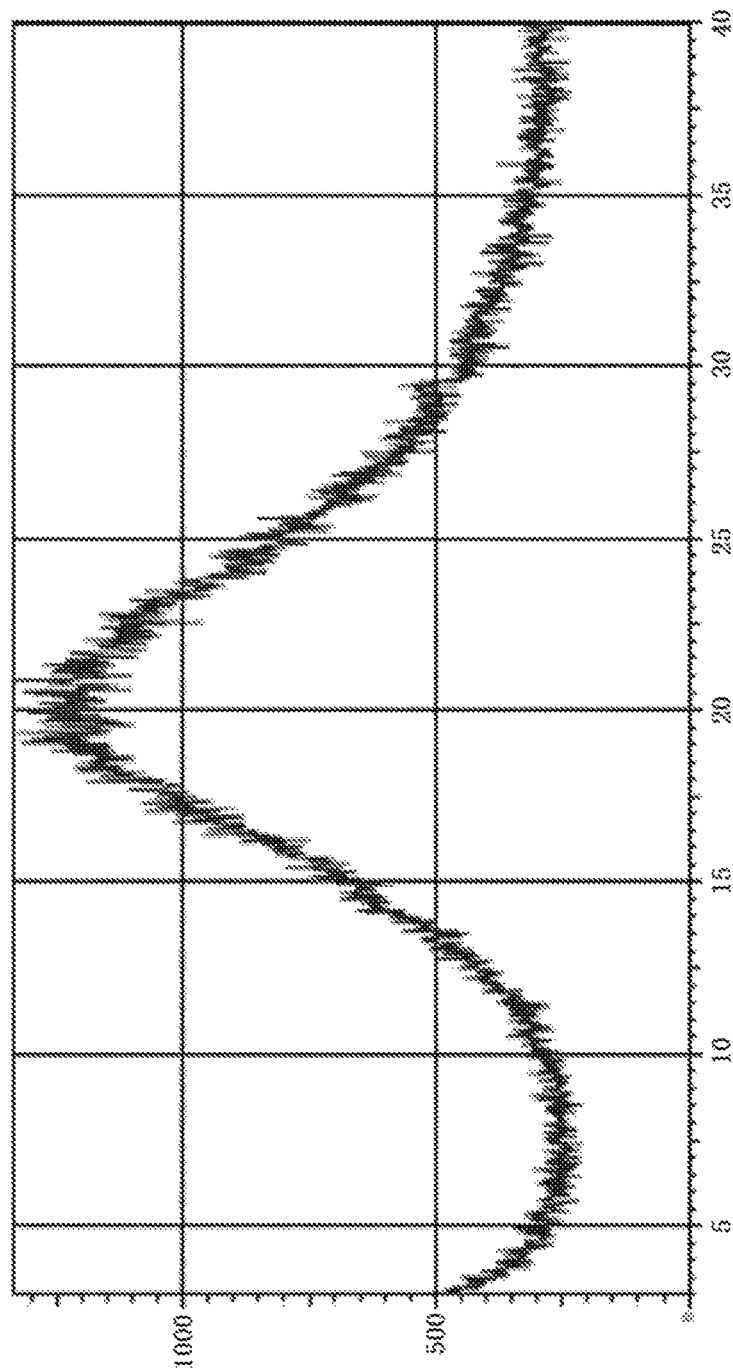
FIG. 6 is an X-ray powder diffraction (XRPD) pattern of an amorphous form of brexpiprazole free base reported in CN 201510180947.

0.2 g of brexpiprazole was added to 6 ml of dichloromethane, treated by ultrasonication, stirred until completely dissolved to obtain a clarified solution, and evaporated to dryness under reduced pressure at room temperature, to give an amorphous brexpiprazole solid with HPLC of 99.64%. The X-ray powder diffraction pattern of the amorphous solid obtained was detected and shown in FIG. 6.

The comparison of the stability of brexpiprazole in the crystal form I, the dihydrated crystal form, the anhydrous crystal form and the amorphous form is shown in Table 1. The test in Table 1 was carried out at 25° C. and 60% ambient humidity.

TABLE 1

| Brexpiprazole crystal form | Water Content (initial), wt. % | Water Content (after 1 month), wt. % | Water Content (after 2 months), wt. % | Water Content (after 3 months), wt. % |
|---|---|---|---|---|
| Crystal form I | 1.24 | 1.27 | 1.26 | 1.27 |
| Dihydrated crystal form | 6.74 | 6.90 | 7.10 | 7.50 |
| Anhydrous crystal form | 0.02 | 0.09 | 0.21 | 0.30 |
| Amorphous form | 0.02 | 0.13 | 0.22 | 0.40 |

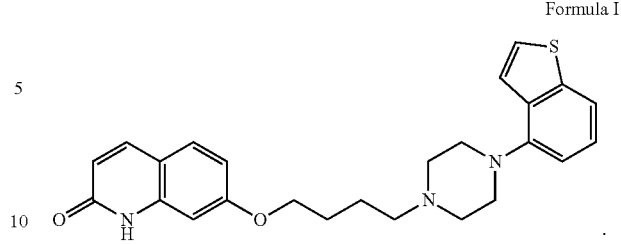

Formula I

The invention claimed is:

1. A crystal form I of brexpiprazole having a structure of formula I, wherein an X-ray powder diffraction pattern of the crystal form I comprises characteristic peaks of 9.1±0.2, 10.8±0.2, 14.9±0.2, 15.2±0.2, 15.7±0.2, 16.5±0.2, 17.6±0.2, 18.1±0.2, 18.6±0.2, 24.4±0.2 degrees 2θ, 2. The crystal form I of brexpiprazole of claim 1, wherein the crystal form I has a crystal water endothermic peak at about 43° C.-72° C. and a melting endothermic peak at 179° C.-184° C. exhibited by a differential scanning calorimetry pattern.

3. The crystal form I of brexpiprazole of claim 1, wherein the crystal form I has a water content of 3.0 wt. %-4.0 wt. %.

4. A method for preparing the crystal form I of brexpiprazole having the structure of formula I of claim 1, comprising following steps:
    (a) mixing brexpiprazole with a mixed solvent of ethanol and water at room temperature to prepare a suspension;
    (b) adding acetic acid into the suspension of step (a) and heating to completely dissolved to obtain a clarified solution; and
    (c) adding the clarified solution of step (b) into a sodium hydroxide solution to pH of 7-14 after cooling, precipitating solids, keeping stirring, filtering and drying to obtain the crystal form I of brexpiprazole.

5. The method of claim 4, wherein a ratio of ethanol to water in step (a) is 2:3.

6. The method of claim 4, wherein the clarified solution of step (b) is added into the sodium hydroxide solution to pH of 10-11 after cooling in step (c).

7. The crystal form I of brexpiprazole of claim 2, wherein the crystal form I has a water content of 3.0 wt. %-4.0 wt. %.

* * * * *